United States Patent
Ikeda et al.

(10) Patent No.: US 10,625,492 B2
(45) Date of Patent: Apr. 21, 2020

(54) METHOD FOR PRODUCING MEDIUM AND FIBER ASSEMBLY, AND APPARATUS FOR PRODUCING MEDIUM

(71) Applicant: Panasonic Intellectual Property Management Co., Ltd., Osaka (JP)

(72) Inventors: Kouji Ikeda, Hyogo (JP); Taichi Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 292 days.

(21) Appl. No.: 15/623,912

(22) Filed: Jun. 15, 2017

(65) Prior Publication Data
US 2018/0015700 A1 Jan. 18, 2018

(30) Foreign Application Priority Data

Jul. 13, 2016 (JP) .................................. 2016-138327
Jan. 26, 2017 (JP) .................................. 2017-012363

(51) Int. Cl.
| | | |
|---|---|---|
| *B32B 25/20* | (2006.01) | |
| *B32B 5/02* | (2006.01) | |
| *B32B 37/12* | (2006.01) | |
| *B32B 37/06* | (2006.01) | |
| *B32B 7/12* | (2006.01) | |
| *B32B 37/15* | (2006.01) | |

(Continued)

(52) U.S. Cl.
CPC ................ *B32B 25/20* (2013.01); *B32B 5/02* (2013.01); *B32B 7/12* (2013.01); *B32B 37/0053* (2013.01); *B32B 37/025* (2013.01); *B32B 37/06* (2013.01); *B32B 37/12* (2013.01); *B32B 37/153* (2013.01); *B29C 53/60* (2013.01); *B29C 53/62* (2013.01); *B29C 69/003* (2013.01); *B32B 2535/00* (2013.01); *C12N 5/0018* (2013.01); *C12N 5/0062* (2013.01)

(58) Field of Classification Search
CPC ..... B29C 53/56; B29C 53/562; B29C 53/564; B29C 53/58; B29C 53/60; B29C 53/62; B29C 69/003; C12N 5/0018; C12N 5/0062
USPC .......................................................... 156/174
See application file for complete search history.

(56) References Cited

U.S. PATENT DOCUMENTS

2007/0045175 A1* 3/2007 Jang .................. B01D 67/0088
210/500.36
2008/0194010 A1 8/2008 Liu
(Continued)

FOREIGN PATENT DOCUMENTS

JP 2008-502813 A 1/2008
JP 2008-540868 A 11/2008
(Continued)

*Primary Examiner* — Carson Gross
(74) *Attorney, Agent, or Firm* — Pearne & Gordon LLP

(57) ABSTRACT

A method for producing a medium includes forming a fiber assembly by discharging a raw material liquid of fibers from a nozzle to generate the fibers and depositing the fibers so as to surround a circumferential surface of a rotatable winder, and transferring the fiber assembly to a base member while rotating the rotatable winder. The circumferential surface of the rotatable winder has a plurality of belt-shaped projection portions extending in a direction along a rotation axis of the rotatable winder.

15 Claims, 15 Drawing Sheets

(51) Int. Cl.
B32B 37/00 (2006.01)
B29C 53/62 (2006.01)
C12N 5/00 (2006.01)
B29C 69/00 (2006.01)
B29C 53/60 (2006.01)

(56) References Cited

U.S. PATENT DOCUMENTS

2008/0241538 A1* 10/2008 Lee .................. D01D 5/0076
428/401
2009/0117380 A1  5/2009 Lee et al.

FOREIGN PATENT DOCUMENTS

JP  2009-084757 A  4/2009
JP  2010-517590 A  5/2010

* cited by examiner

METHOD FOR PRODUCING MEDIUM AND FIBER ASSEMBLY, AND APPARATUS FOR PRODUCING MEDIUM

BACKGROUND

1. Technical Field

The disclosure relates to a method for producing a medium and a fiber assembly, and an apparatus for producing a medium, and particularly, relates to an improvement of productivity of a medium and a fiber assembly including fibers arranged in one direction.

2. Description of the Related Art

In recent years, as a medium for cultivating biological tissues or microorganisms, a fiber base member attracts attention (see PCT Japanese Translation Patent Publication No. 2010-517590). The fiber base member is, for example, a woven fiber, a knitted fiber, or a nonwoven fiber, and has a three-dimensional structure. Therefore, it is possible to cultivate the biological tissues or the microorganisms in a state close to a physiological environment in vitro.

SUMMARY

A method for producing a medium according to one aspect of the disclosure includes forming a fiber assembly by discharging a raw material liquid of fibers from a nozzle to generate the fibers and depositing the fibers so as to surround a circumferential surface of a rotatable winder; and transferring the fiber assembly to a base member while rotating the rotatable winder. The circumferential surface of the rotatable winder has a plurality of belt-shaped projection portions extending in a direction along a rotation axis of the rotatable winder.

A method for producing a fiber assembly according to another aspect of the disclosure is a method for producing a fiber assembly including a plurality of fibers arranged in one direction, the method includes preparing a raw material liquid of the fibers; and depositing the fibers generated by discharging the raw material liquid of the fibers from a nozzle so as to surround a circumferential surface of a rotatable winder.

An apparatus for producing a medium according to further another aspect of the disclosure includes a nozzle that discharges a raw material liquid of fibers to generate the fibers; a rotatable winder that forms a fiber assembly by depositing the fibers so as to surround a circumferential surface; and a pedestal on which a base member to which the fiber assembly is transferred while the rotatable winder is rotated is placed. The rotatable winder has a plurality of belt-shaped projection portions extending in a direction along a rotation axis of the rotatable winder on the circumferential surface of the rotatable winder.

According to the producing method and the producing apparatus of the disclosure, it is possible to efficiently produce the medium and the fiber assembly including the fibers arranged in one direction.

DETAILED DESCRIPTIONS

Prior to the explanation of the embodiments, problems in the related art will be briefly described.

In a case where a direction is observed in the growth of biological tissues or microorganisms, it is desirable that fibers constituting a fiber base member are arranged in one direction. This is because the biological tissues have an arrangement property.

A fiber assembly formed on a circumferential surface of a rotatable winder is useful as a medium having a high arrangement property by winding up the fibers with the rotatable winder while spinning the fibers. However, it is not easy to transfer the medium to the base member while maintaining the arrangement property. This is because the fibers are not entangled with each other to such an extent that the arrangement can be maintained when the fiber assembly is peeled off from the rotatable winder.

Figure 1A:
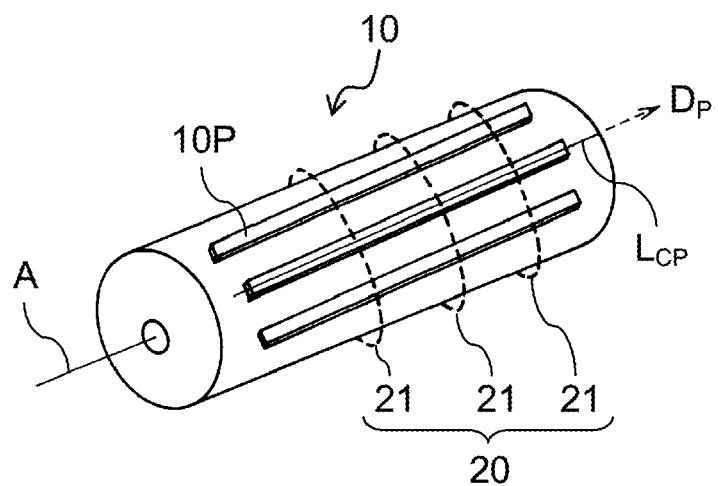
FIG. 1A is a perspective view illustrating an example of a rotatable winder according to the disclosure.
Figure 1B:
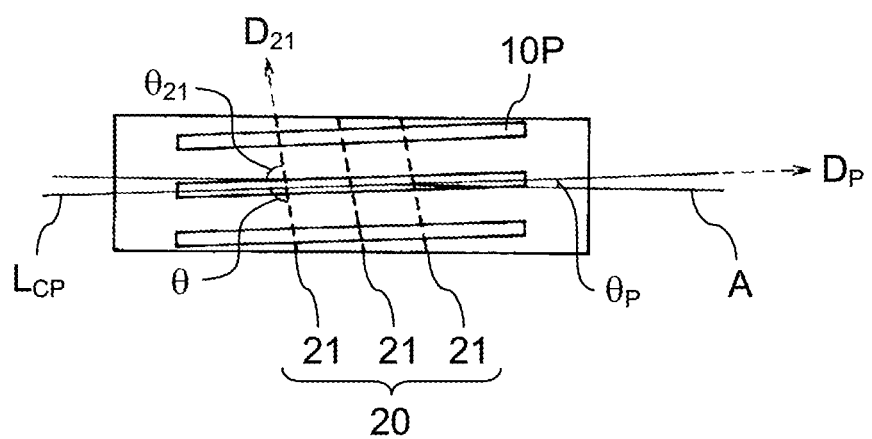
FIG. 1B is a plan view illustrating an example of the rotatable winder according to the disclosure.

In the embodiment, in a state where the arrangement of the fibers in one direction is maintained, in order that the fiber assembly is transferred to the base member, as illustrated in FIGS. 1A and 1B, a plurality of belt-shaped projection portions 10P extending in a direction along rotation axis A of rotatable winder 10 are disposed on a circumferential surface of rotatable winder 10. Therefore, an assembly (fiber assembly 20) of fibers 21 arranged so as to surround the circumferential surface of rotatable winder 10 is easily peeled off from rotatable winder 10. As a result, it is possible to easily transfer fiber assembly 20 to the base member while maintaining the arrangement of fibers 21. FIG. 1A is a perspective view illustrating an example of rotatable winder 10 and FIG. 1B is a plan view thereof. FIGS. 1A and 1B also illustrate a part of fiber assembly 20 deposited on the circumferential surface of rotatable winder 10.

Fibers 21 are deposited on the circumferential surface of rotatable winder 10 while being arranged in a direction (hereinafter, arrangement direction $D_{21}$) surrounding the circumferential surface of rotatable winder 10. Arrangement direction $D_{21}$ is, for example, a direction along a rotating direction (that is, a direction perpendicular to rotation axis A of rotatable winder 10).

Angle $\theta_{21}$ ($\theta_{21} \leq 90°$) formed by arrangement direction $D_{21}$ and rotation axis A may be, for example, 60° or more and 90° or less. Arrangement direction $D_{21}$ is a longitudinal direction of fiber 21 when fiber 21 is viewed from a normal direction of the circumferential surface of rotatable winder 10 (see FIG. 1B). The longitudinal direction of fiber 21 may be obtained by taking an approximate straight line of fiber 21 when viewed from the normal direction of the circumferential surface of rotatable winder 10. Angle $\theta_{21}$ is an average value of angles formed by arrangement directions $D_{21}$ of a plurality of fibers 21 and rotation axis A. Arrangement directions $D_{21}$ of the plurality of fibers 21 deposited on rotatable winder 10 may be different from each other within the range described above.

Projection portion 10P is belt-like shaped and extends in the direction (hereinafter, extending direction $D_P$) along rotation axis A of rotatable winder 10 in the circumferential surface of rotatable winder 10. Extending direction $D_P$ is not limited to a case where it is parallel to rotation axis A and angle $\theta_P$ ($\theta_P < 90°$) formed by extending direction $D_P$ and rotation axis A is, for example, 0° or more and 30° or less. In particular, from the viewpoint of a peeling property of fiber assembly 20, it is preferable that angle $\theta_P$ is 0° or more and 20° or less.

Extending direction $D_P$ is a direction intersecting arrangement direction $D_{21}$ of fibers 21. Angle $\theta$ ($\theta \leq 90°$) formed by extending direction $D_P$ and arrangement direction $D_{21}$ is, for example, 60° or more and 90° or less. Extending direction $D_P$ is a direction in which center line $L_{CP}$ of projection portion 10P in the longitudinal direction extends when projection portion 10P is viewed from the normal direction of the circumferential surface of rotatable winder 10. In a case where center line $L_{CP}$ is a curved line, extending direction $D_P$ is a direction in which a center line of the smallest rectangle surrounding center line $L_{CP}$ extends. Extending direction $D_R$ of rib 10R which is described below can be obtained in the same manner.

The shape of projection portion 10P is not particularly limited to the belt-like shape. The belt-like shape is a shape in which a length of projection portion 10P in extending direction $D_P$ is longer than a length in a direction perpendicular to extending direction $D_P$. Examples of the shape of projection portion 10P when viewed from the normal direction of the circumferential surface of rotatable winder 10 include a rectangular shape, a trapezoidal shape, and the like.

The number of projection portions 10P is not particularly limited, and may be two or more. In particular, from the viewpoint of the peeling property of fiber assembly 20, it is preferable that three or more projection portions 10P are disposed and it is preferable that ten or more projection portions 10P are disposed on the circumferential surface of rotatable winder 10. From the same viewpoint, it is preferable that projection portions 10P are disposed at regular intervals. As described below, in a case where fiber assembly 20 is cut in a state of being wound around rotatable winder 10 before a transfer step of fiber assembly 20 to base member 30 (see FIG. 9C), fiber assembly 20 is cut between projection portions 10P so that at least a part of fiber assembly 20 after cutting is in a state of being in contact with projection portions 10P. Therefore, the arrangement of fibers 21 is easily maintained. In this case, it is preferable that an interval of planned cutting point C (see FIG. 2) between projection portions 10P is smaller than intervals of other portions between projection portions 10P.

A length (width) of projection portion 10P in a lateral direction is not particularly limited. In particular, from the viewpoint of the peeling property of fiber assembly 20, it is preferable that the width of each projection portion 10P is determined so that a total area of all projection portions 10P abutting against the circumferential surface of rotatable winder 10 is 10% or more and 80% or less, and particularly; 30% or more and 70% or less of a surface area of the circumferential surface of rotatable winder 10. The length of projection portion 10P in extending direction $D_P$ is not particularly limited. In particular, it is preferable that projection portions 10P extend over a region in which at least fibers 21 can be deposited on the circumferential surface of rotatable winder 10.

A height of projection portion 10P is not particularly limited. In particular, it is preferable that the height of projection portion 10P is not excessively high in that slackness of fibers 21 is suppressed and the arrangement in one direction is easily maintained. From the viewpoint of the peeling property of fiber assembly 20 and slackness suppression of fibers 21, it is preferable that the height of projection portion 10P is 100 to 5,000 μm. The height of projection portion 10P is an average value in the normal direction of the circumferential surface of rotatable winder 10.

A material of projection portion 10P is not particularly limited and various resin materials can be exemplified. In particular, it is preferable that projection portion 10P includes a silicone rubber layer at least at a contact portion with fibers 21. This is because the peeling property of fiber assembly 20 is further improved. Since silicone rubber has an appropriate adhesive property; peeling of fiber assembly 20 from the circumferential surface of rotatable winder 10 before the transfer step is suppressed.

Silicone rubber is a non-thermoplastic compound of which a main chain is formed by a silicon-oxygen bond (siloxane bond). Examples of the silicone rubber include methyl silicone rubber, vinyl-methyl silicone rubber, phenyl-methyl silicone rubber, dimethyl silicone rubber, fluorosilicone rubber, and the like. Of course, all projection portions 10P may be formed of the silicone rubber. As described below, in a case where fibers 21 are produced by an electrospinning method, it is preferable that projection portions 10P have conductivity.

Figure 2:
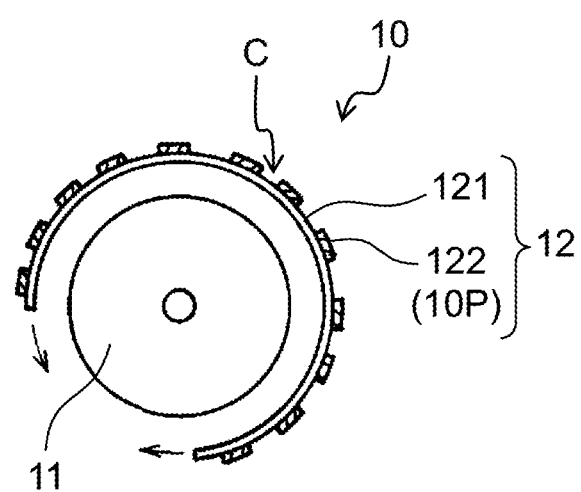
FIG. 2 is an exploded side view illustrating another example of a rotatable winder according to the disclosure.

From the viewpoint of a handling property, it is preferable that projection portions 10P are disposed in a detachable state on rotatable winder 10. For example, as illustrated in FIG. 2, uneven sheet 12 including supporting sheet 121 and silicone rubber 122 disposed in a belt-like shape on a surface of supporting sheet 121 is prepared, and uneven sheet 12 may be wound around rotation base body 11. In this case, silicone rubber 122 corresponds to projection portion 10P. With the configuration, it is easy to arrange projection portions 10P and to replace projection portions 10P in a case of being deteriorated.

A material of supporting sheet 121 is not particularly limited and, for example, includes polyester such as polyethylene terephthalate (PET), polyimide, or the like. In a case where fibers 21 are produced by the electrospinning method, it is preferable that supporting sheet 121 is also electrically conductive. A thickness of supporting sheet 121 is not particularly limited and may be appropriately set according to the material of supporting sheet 121 or the like. As silicone rubber 122, the compounds described above can be exemplified.

Figure 3:
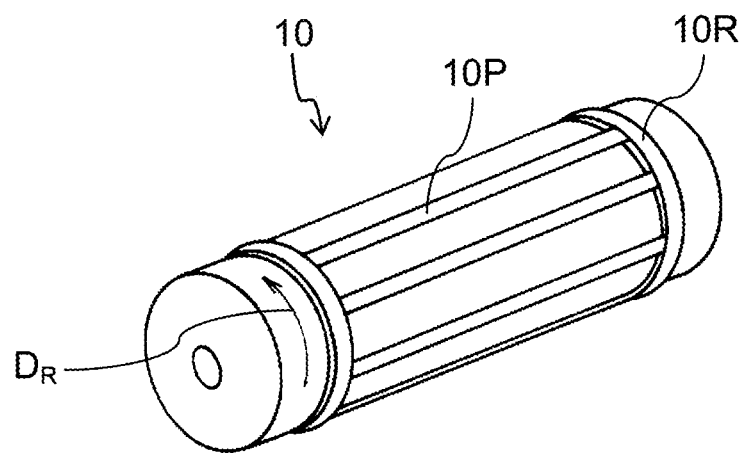
FIG. 3 is a perspective view illustrating further another example of a rotatable winder according to the disclosure.

As illustrated in FIG. 3, it is preferable that ribs 10R extending in a direction intersecting rotation axis A are disposed on the circumferential surface of rotatable winder 10 in that the arrangement of fibers 21 is easily maintained during the transfer step to base member 30.

Figure 15A:
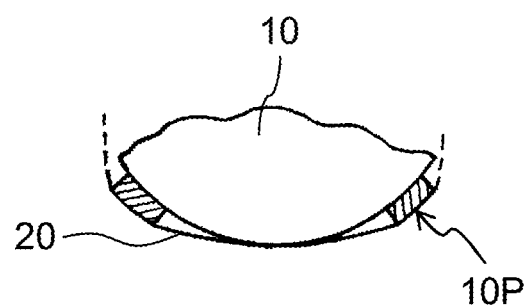
FIG. 15A is a side view schematically illustrating a part of the rotatable winder and the base member in the transfer step.
Figure 15B:
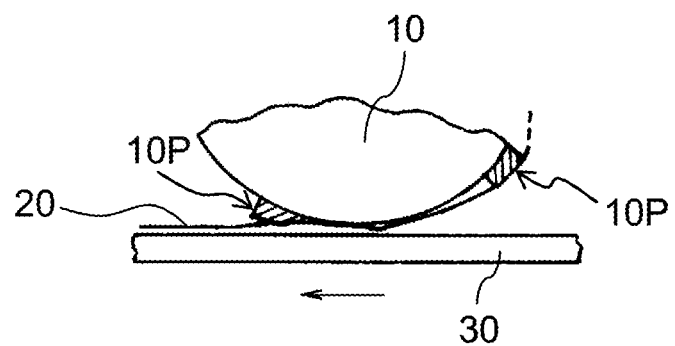
FIG. 15B is a side view schematically illustrating a part of the rotatable winder and the base member in the transfer step.

The transfer step is performed while rotating rotatable winder 10. Fiber assembly 20 formed on the circumferential surface of rotatable winder 10 or the surface of projection portion 10P sequentially abuts against base member 30. Therefore, fiber assembly 20 is transferred to base member 30. As illustrated in FIG. 15A, fiber assembly 20 is formed in a state of floating from the circumferential surface of rotatable winder 10 in the vicinity of the plurality of projection portions 10P. As illustrated in FIG. 15B, when transferring, projection portions 10P are deformed by abutting against base member 30. Therefore, slackness easily occurs in fiber assembly 20 floated in the vicinity of projection portions 10P and the arrangement of fibers 21 may be disturbed by the transfer.

In a case where ribs 10R are disposed, base member 30 does not abut against the circumferential surface of rotatable winder 10 but abuts against ribs 10R. Therefore, a degree of deformation of projection portions 10P is reduced. Thus, the slackness of fiber assembly 20 generated during transferring is suppressed and the arrangement property of fibers 21 is maintained. From the viewpoint of suppressing the deformation of projection portions 10P in the transfer step, it is preferable that a height of rib 10R is equal to or greater than the height of projection portion 10P.

For example, as illustrated in FIG. 3, rib 10R extends in the direction intersecting rotation axis A. In FIG. 3, ribs 10R are disposed in the vicinity of end portions of rotatable winder 10 so as to surround the circumferential surface of rotatable winder 10 along the rotating direction and to connect the end portions of the plurality of projection portions 10P. An angle (≤90°) formed by extending direction $D_R$ of rib 10R and rotation axis A is, for example, 60° or more and 90° or less.

Rib 10R is not limited to the shape illustrated in FIG. 3. For example, when rotatable winder 10 is viewed from the direction of rotation axis A, ribs 10R may be intermittently disposed so as to fill a space between projection portions 10P. Although the number of ribs 10R is not particularly limited, from the viewpoint of stability of the transfer, it is preferable that the number thereof is two or more. The material of rib 10R is not particularly limited and may be the same as that of projection portion 10P.

Figure 4A:
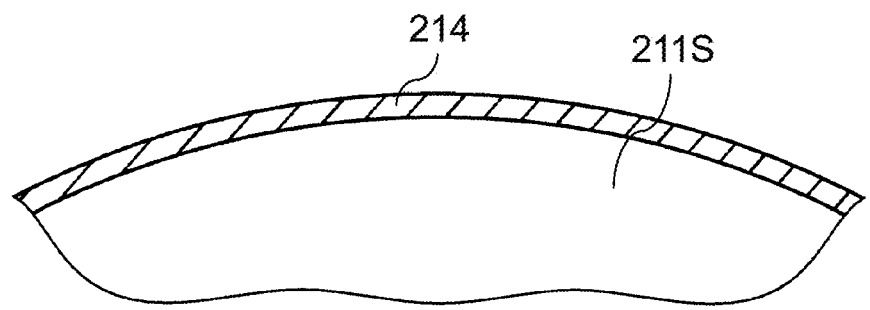
FIG. 4A is a side view of a main portion schematically illustrating an example of a rotation base body in each step of a method for obtaining a rotatable winder including projection portions on a circumferential surface using ribs formed between a plurality of grooves of the rotation base body.
Figure 4B:
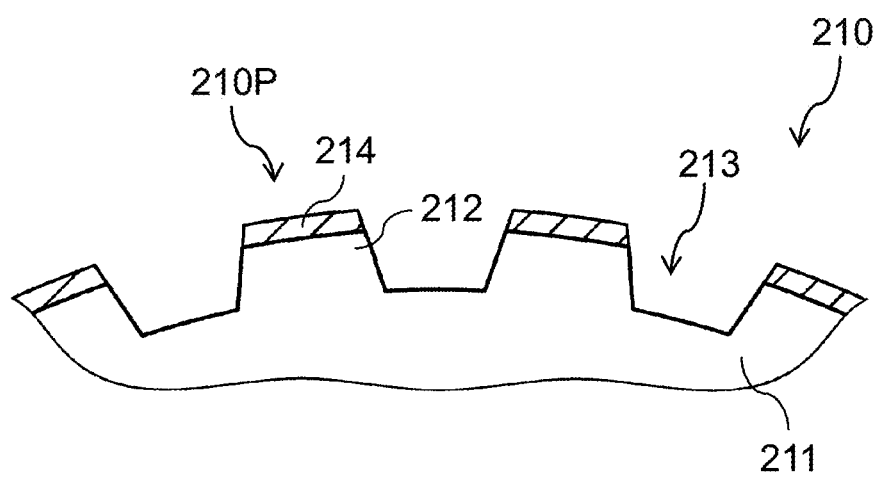
FIG. 4B is a side view of a main portion schematically illustrating an example of the rotation base body in each step of the method for obtaining the rotatable winder including the projection portions on the circumferential surface using the ribs formed between the plurality of grooves of the rotation base body.

As illustrated in FIG. 4B, it is preferable that rotatable winder 210 having a plurality of projection portions 210P on a circumferential surface includes rotation base body 211. Rotation base body 211 includes a plurality of grooves 213 extending in a direction along a rotation axis of rotation base body 211 on a surface (circumferential surface) thereof, and rib 212 is formed between grooves 213 adjacent to each other. That is, a plurality of ribs 212 and grooves 213 extending in the direction along the rotation axis of rotation base body 211 are alternately formed on the circumferential surface of rotation base body 211. Rib 212 constitutes a part of projection portion 210P. As illustrated in FIG. 4B, projection portion 210P includes silicone rubber layer 214. In this case, it is possible to form projection portion 210P with a large height on the circumferential surface of rotatable winder 210 by using rib 212 without increasing a thickness of silicone rubber layer 214. The thickness of silicone rubber layer 214 is, for example, 0.01 to 3 mm. The height of projection portion 210P is, for example, 1 to 15 mm.

If the thickness of the silicone rubber layer is increased in order to facilitate peeling of the fiber assembly from the rotatable winder, a side surface of the silicone rubber layer increases and air resistance received by the side surface of the silicone rubber layer due to the rotation of the rotatable winder increases. In addition, a weight of the silicone rubber layer increases and a centrifugal force exerted on the silicone rubber layer during the rotation of the rotatable winder increases. On the other hand, it is possible to reduce the air resistance received by the side surface of silicone rubber layer 214 or the centrifugal force exerted on silicone rubber layer 214, and to suppress peeling of silicone rubber layer 214 by making silicone rubber layer 214 thin using rib 212.

Hereinafter, an example of a method for obtaining the rotatable winder including the projection portions on the circumferential surface using the ribs formed between the plurality of grooves of the rotation base body. First, as illustrated in FIG. 4A, silicone rubber layer 214 is formed on a smooth circumferential surface of columnar body 211S which is a precursor of rotation base body 211 using a film forming technique. Next, as illustrated in FIG. 4B, the circumferential surface of columnar body 211S is scraped together with silicone rubber layer 214 and grooves 213 extending in the direction along the rotation axis of columnar body 211S is formed. The same operation is repeated at predetermined intervals along the circumferential surface of columnar body 211S. As described above, it is possible to obtain rotation base body 211 in which the plurality of ribs 212 and grooves 213 are alternately formed on the circumferential surface, and to form the plurality of projection portions 210P including ribs 212 and silicone rubber layers 214 between grooves 213 adjacent to each other. That is, it is possible to obtain rotatable winder 210 including projection portions 210P on the circumferential surface. In the above description, instead of forming silicone rubber layer 214 on the surface of columnar body 211S using the film forming technique, a composite sheet including a supporting sheet (PET sheet or the like) and a silicone rubber layer disposed on a surface of the supporting sheet may be attached to the circumferential surface of columnar body 211S using adhesive or the like.

Hereinafter, another example of a method for obtaining a rotatable winder including projection portions on a circumferential surface using ribs formed between a plurality of grooves of a rotation base body will be described below.

Figure 5A:
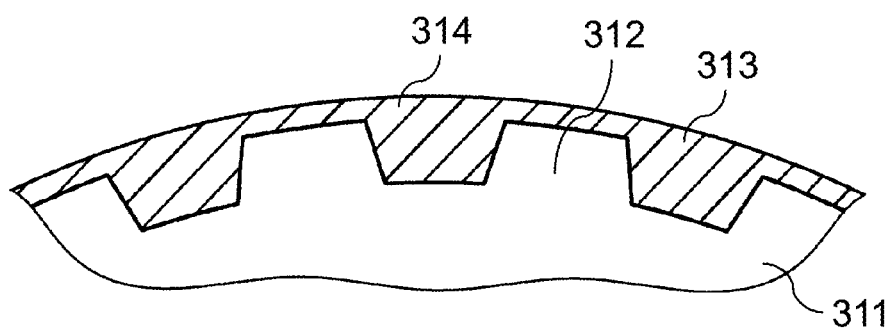
FIG. 5A is a side view of a main portion schematically illustrating another example of a rotation base body in each step of a method for obtaining a rotatable winder including projection portions on a circumferential surface using ribs formed between a plurality of grooves of the rotation base body.
Figure 5B:
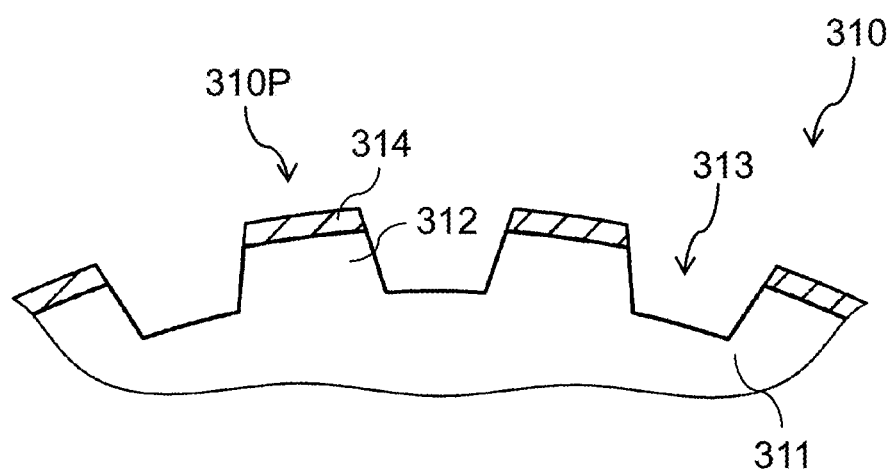
FIG. 5B is a side view of a main portion schematically illustrating another example of a rotation base body in each step of the method for obtaining the rotatable winder including the projection portions on the circumferential surface using the ribs formed between the plurality of grooves of the rotation base body.

As illustrated in FIG. 5A, rotation base body 311, in which a plurality of ribs 312 and grooves 313 extending in a direction along a rotation axis of rotation base body 311 are alternately formed on the circumferential surface, is prepared and silicone rubber layer 314 is formed on a circumferential surface of rotation base body 311 using a film forming technique. Next, as illustrated in FIG. 5B, portions formed in the plurality of grooves 313 in silicone rubber layer 314 are scraped. As described above, it is possible to form a plurality of projection portions 310P including ribs 312 and silicone rubber layers 314 between grooves 313 adjacent to each other. That is, it is possible to obtain rotatable winder 310 including the plurality of projection portions 310P on the circumferential surface.

Figure 6:
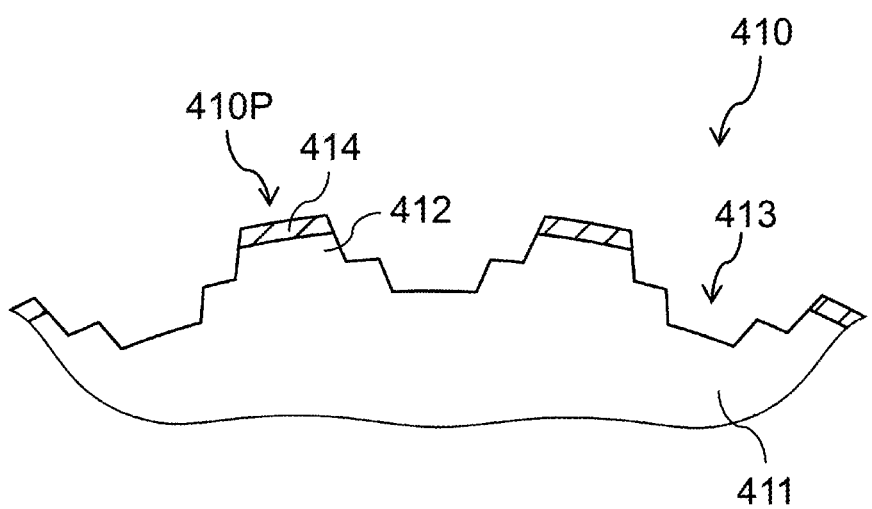
FIG. 6 is a side view of a main portion illustrating an example of a rotatable winder including projection portions on a circumferential surface obtained using ribs formed between a plurality of grooves of a rotation base body.

Instead of rotation base body 311, rotation base body 411 illustrated in FIG. 6 may be used. Rotation base body 411 alternately includes ribs 412 and grooves 413 having a projection shape of two steps on the circumferential surface thereof.

As illustrated in FIG. 6, it is possible to form a plurality of projection portions 410P including ribs 412 and silicone rubber layers 414 having the projection shape of two steps between grooves 413 adjacent to each other. That is, it is possible to obtain rotatable winder 410 including the plurality of projection portions 410P on the circumferential surface. The fiber assembly can be more easily peeled off from rotatable winder 410 by making ribs 412 in the projection shape of two steps.

Figure 7:
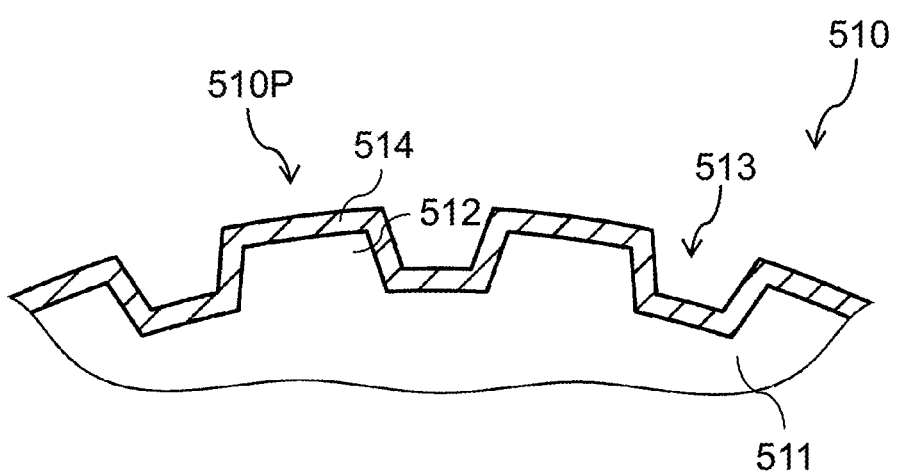
FIG. 7 is a side view of a main portion illustrating another example of a rotatable winder including projection portions on a circumferential surface obtained using ribs formed between a plurality of grooves of a rotation base body.

As illustrated in FIG. 7, rotation base body 511, in which a plurality of ribs 512 and grooves 513 extending in a direction along a rotation axis of rotation base body 511 are alternately formed on the circumferential surface, is prepared and composite sheet 514 may be attached to the entirety of the circumferential surface of rotation base body 511 using adhesive or the like. Composite sheet 514 includes a supporting sheet (PET sheet or the like) and a silicone rubber layer disposed on a surface of the supporting sheet. In this case, it is possible to form a plurality of projection portions 510P including ribs 512 and composite sheet 514 between grooves 513 adjacent to each other. That is, it is possible to obtain rotatable winder 510 including the plurality of projection portions 510P on the circumferential surface. In this case, composite sheet 514 is disposed on not only surfaces of the plurality of ribs 512 but also surfaces of grooves 513 formed between ribs 512 adjacent to each other.

In the above description, portions disposed on the surfaces of the plurality of grooves 513 in composite sheet 514 disposed on the circumferential surface of rotation base body 511 may be scraped. Composite sheet 514 may also be attached to only the surfaces of the plurality of ribs 512 of rotation base body 511. However, it is more convenient to attach composite sheet 514 to the entire circumferential surface of rotation base body 511. In a case where composite sheet 514 is attached to the entire circumferential surface of rotation base body 511, the silicone rubber layer does not fall off from the rotatable winder due to the air resistance received by the side surface of the silicone rubber layer during rotation of the rotatable winder.

Figure 8:
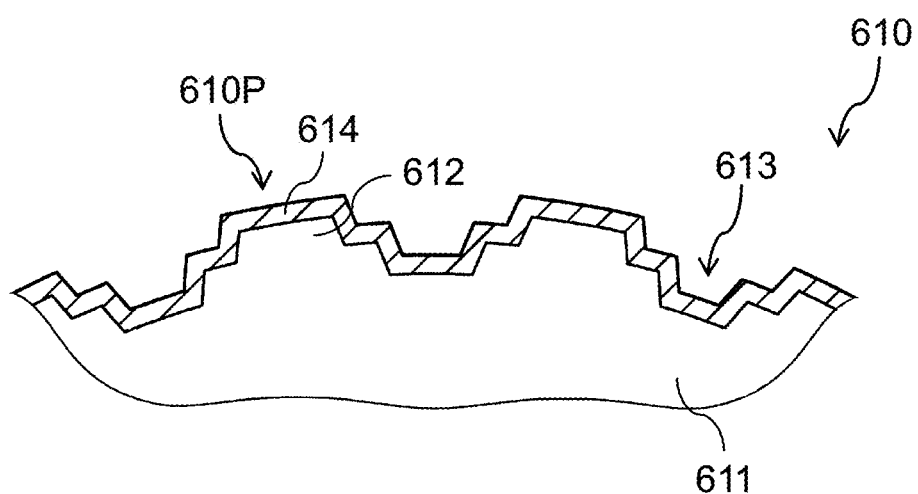
FIG. 8 is a side view of a main portion illustrating further another example of a rotatable winder including projection portions on a circumferential surface obtained using ribs formed between a plurality of grooves of a rotation base body.

Instead of rotation base body 511, rotation base body 611 illustrated in FIG. 8 may be used. Rotation base body 611 alternately includes ribs 612 having a projection shape of two steps and grooves 613 on the circumferential surface thereof. As illustrated in FIG. 8, it is possible to form a plurality of projection portions 610P including ribs 612 having the projection shape of two steps and composite sheet 614 between grooves 613 adjacent to each other by attaching composite sheet 614 having the same configuration as that of composite sheet 514 to an entirety of the circumferential surface of rotation base body 611. That is, it is possible to obtain rotatable winder 610 including the plurality of projection portions 610P on the circumferential surface.

Hereinafter, an embodiment using rotatable winder 10 will be described in detail with reference to the drawings.

The method for producing a medium according to the embodiment includes a deposition step in which fibers 21 are generated by discharging a raw material liquid of fibers 21 from a nozzle and fibers 21 are deposited so as to surround the circumferential surface of rotatable winder 10 to form fiber assembly 20, and a transfer step of transferring fiber assembly 20 to base member 30 while rotating rotatable winder 10.

The producing method described above produces a medium using an apparatus including a nozzle that discharges the raw material liquid of fibers 21 to generate fibers 21, rotatable winder 10 that forms fiber assembly 20 by depositing fibers 21 so as to surround the circumferential surface, and pedestal 53 on which base member 30 to which fiber assembly 20 is transferred while rotatable winder 10 is rotated is placed.

In the embodiment, fiber assembly 20 is produced by a method including a step of preparing raw material liquid 22 of fibers 21, and a deposition step in which fibers 21 are generated by discharging the raw material liquid of fibers 21 from a nozzle and fibers 21 are deposited so as to surround the circumferential surface of rotatable winder 10. Fiber assembly 20 formed on the circumferential surface of rotatable winder 10 is transferred to a release paper as required. Fiber assembly 20 can be used alone as a medium.

Figure 9A:
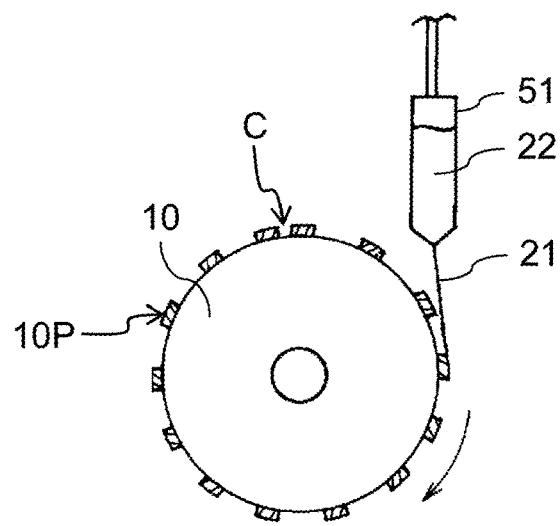
FIG. 9A is a side view schematically illustrating a rotatable winder and a base member in each step of a producing method according to the disclosure.
Figure 9B:
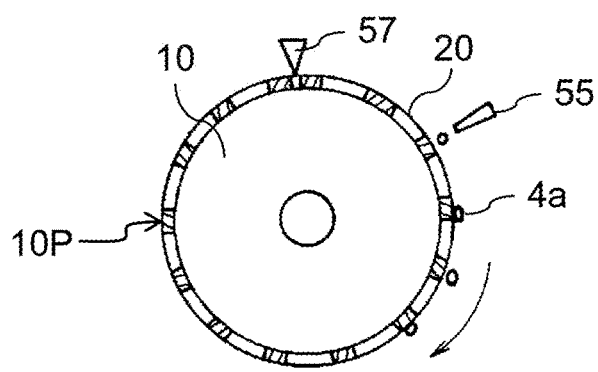
FIG. 9B is a side view schematically illustrating the rotatable winder and the base member in each step of the producing method according to the disclosure.
Figure 9C:
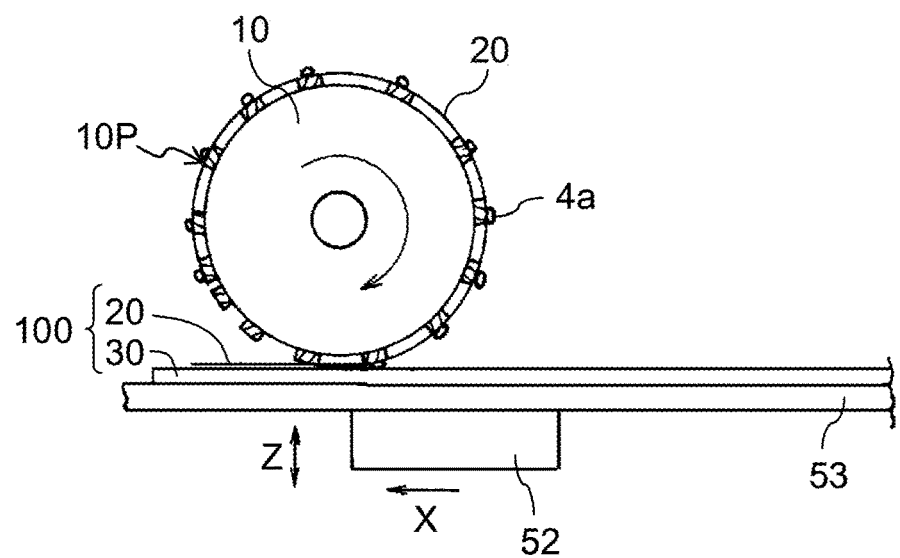
FIG. 9C is a side view schematically illustrating the rotatable winder and the base member in each step of the producing method according to the disclosure.

Hereinafter, the producing method and the producing apparatus according to the embodiment will be described in detail mainly with reference to FIGS. 9A to 9C. FIGS. 9A to 9C are side views schematically illustrating rotatable winder 10, base member 30, and the like in each step of the embodiment.

1. Deposition Step (FIG. 9A)

In the step, raw material liquid 22 of fiber 21 is prepared, fiber 21 is generated from raw material liquid 22, and fiber 21 is deposited while surrounding the circumferential surface of rotatable winder 10 for one turn or more. Therefore, fiber assembly 20 is formed on the circumferential surface of rotatable winder 10.

The method (spinning method) for producing fiber 21 from raw material liquid 22 is not particularly limited and may be appropriately selected according to a kind of generated fiber 21 or the like. Examples of the spinning method include a solution spinning method, a melt spinning method, an electrospinning method, and the like.

The solution spinning method is a method in which solution obtained by dissolving the raw material of fiber 21 in a solvent is used as raw material liquid 22. The solution spinning method using solvent includes a so-called wet spinning method and a dry spinning method. In the wet spinning method, fibers are formed by discharging raw material liquid 22 into a coagulating liquid by a chemical reaction between the raw material of fibers 21 and the coagulating liquid, or by replacing the solvent with the coagulating liquid. In the dry spinning method, after discharging raw material liquid 22 into the air, the solvent is removed by heating or the like, and whereby fibers 21 are formed. Among them, the dry spinning method is preferable in that it is easy to deposit fibers 21 in a state of being arranged in one direction.

The melt spinning method is a method in which a melt liquid obtained by heating and melting the raw material of fiber 21 is used as raw material liquid 22. The obtained raw material liquid 22 is discharged into the air and then cooled to be solidified into a fibrous state. In this case, usually, a solvent for dissolving the raw material of fiber 21 is not used. Therefore, the melt spinning method is preferable in that a removing operation of the solvent can be omitted.

In the solution spinning method and the melt spinning method, before the start of the discharge of raw material liquid 22, after a discharge port of nozzle 51 abuts against the circumferential surface of rotatable winder 10 or another member (hereinafter, referred to as a discharge end holding member (not illustrated)), the discharge of raw material liquid 22 is started in this state. Therefore, a discharge end of raw material liquid 22 is secured by the circumferential surface of rotatable winder 10 or the discharge end holding member, and is held as it is. In a case where the discharge end is held on the circumferential surface of rotatable winder 10, fiber 21 is deposited while surrounding the circumferential surface of rotatable winder 10 by rotating rotatable winder 10 while continuing the discharge of raw material liquid 22 as it is. In a case where the discharge end is held by the discharge end holding member, generated fiber 21 is deposited on rotatable winder 10 by moving the discharge port of nozzle 51 from the vicinity of the discharge end holding member to the vicinity of rotating rotatable winder 10 while continuing the discharge of raw material liquid 22 as it is. In this case, for example, raw material liquid 22 is discharged while moving rotatable winder 10 or nozzle 51 in the direction of rotation axis A so that at least a part of the circumferential surface of rotatable winder 10 is covered and fiber assembly 20 including fibers 21 arranged in arrangement direction $D_{21}$ is formed.

The electrospinning method is common to the solution spinning method in that a solution obtained by dissolving the raw material of fiber 21 in a solvent is used as raw material liquid 22. However, in the electrospinning method, raw material liquid 22 is discharged into the air while a high voltage is applied to raw material liquid 22. The solvent contained in raw material liquid 22 volatilizes in the process until the solvent reaches the circumferential surface of rotatable winder 10.

In the electrospinning method, in order to apply a high voltage to raw material liquid 22, raw material liquid 22 is positively or negatively charged. In this case, rotatable winder 10 is grounded or charged to a polarity opposite to that of raw material liquid 22, so that the discharge end of raw material liquid 22 discharged into the air is attracted to rotatable winder 10 and is attached to the circumferential surface thereof. Then, similar to the solution spinning method and the melt spinning method, fibers 21 are deposited while surrounding the circumferential surface of rotatable winder 10 and covers at least a part of the circumferential surface of rotatable winder 10, and fiber assembly 20 including fibers 21 arranged in the arrangement direction $D_{21}$ is formed by rotating rotatable winder 10 while discharging raw material liquid 22.

Raw Material Liquid

Raw material liquid 22 used in the solution spinning method or the electrospinning method contains the raw material of fiber 21 and a solvent. Raw material liquid 22 used in the melt spinning method contains the raw material of melted fibers 21. The raw material of fiber 21 is not particularly limited as long as it can be used as a medium for the biological tissues or the microorganisms. In particular, in view of high affinity with the biological tissues or the microorganisms and difficulty in stressing the biological tissues or the microorganisms during cultivation, it is preferable that the raw material of fibers 21 contains a block polymer containing a polystyrene block and a polybutadiene block, and a styrene resin different from the block polymer.

The block polymer may be, for example, a diblock structure in which a polybutadiene (PB) block and a polystyrene (PS) block are linked to each other, but it is preferable that the block polymer is a polyblock body of a triblock or more in which the PB block and the PS block are alternately linked to each other. From the viewpoint of ensuring the affinity with the styrene resin, it is preferable that the block polymer contains at least the PS block at the end. The PB block increases the flexibility and elongation of obtained fiber 21.

The content of the PB block in the block polymer is, for example, 10% to 30% by mass, preferably 15% to 30% by mass, and more preferably 20% to 30% by mass or 20% to 25% by mass. In a case where the content of the PB block is in such a range, the affinity with the styrene resin is increased, and homogeneous fiber 21 is easily produced. Obtained fiber 21 has high flexibility and elongation. In a case where fibers 21 are produced by the electrospinning method, high spinnabiity is ensured.

As the styrene resin, a polymer different from the above-mentioned block polymer is used. Examples of the styrene resin include polystyrene (styrene homopolymer), a copolymer of styrene and another copolymerizable monomer. The styrene resin may be used singly or in combination of two or more.

From the viewpoint of compatibility of the flexibility of fiber 21 with ease of formation, a mass ratio (=block polymer:styrene resin) of the block polymer and the styrene resin is, for example, 2:1 to 1:5, preferably 1:1 to 1:4. In particular, in the case where fiber assembly 20 is formed by the electrospinning method using a solution, if the mass ratio is within such a range, it is easy to dissolve the block polymer and the styrene resin in the solvent, and it is possible to ensure high spinnability.

The solvent is not particularly limited as long as it can dissolve the raw material of fiber 21 and can be removed by volatilization or the like, and it can be appropriately selected from water and an organic solvent depending on the kind of raw material or manufacturing conditions. As the solvent, an aprotic polar organic solvent is preferable. Examples of such solvents include amides (such as chain or cyclic amide) such as N,N-dimethylformamide (DMF), N,N-dimethylacetamide (DMAc), and N-methyl-2-pyrrolidone (NMP); sulfoxides such as dimethylsulfoxide, and the like. One kind of these solvents may be used alone, or two or more kinds may be used in combination.

A solid content concentration of raw material liquid 22 can be adjusted according to the kind of the solvent or the like, but it is, for example, 5% to 50% by mass, and may be 10% to 30% by mass. Raw material liquid 22 may further contain additives as necessary.

Fiber

Fiber 21 produced from raw material liquid 22 includes the block polymer and the styrene resin, and further includes additives as required. An average fiber diameter of fiber 21 is preferably, for example, 0.5 to 10 μm, more preferably 1 to 5 μm, and particularly preferably 1.5 to 4 μm.

The average fiber diameter is an average value of the diameters of fibers 21. The diameter of fiber 21 is a diameter of a cross section perpendicular to the length direction of fiber 21. In a case where such a cross section is not circular, the maximum diameter may be regarded as the diameter. The width in the direction perpendicular to the length direction of fiber 21 when viewed from the normal direction of one main surface of fiber assembly 20 may be regarded as the diameter of the fiber. The average fiber diameter is, for example, an average value of diameters of arbitrary points of 10 fibers included in fiber assembly 20 at arbitrary points.

Fiber Assembly

Fiber assembly 20 is an assembly of a plurality of fibers 21. In fiber assembly 20, the plurality of fibers 21 are arranged in one direction. The fact that the plurality of fibers 21 are arranged in one direction means that in fiber assembly 20, fibers 21 do not intersect each other or an average angle at which fibers 21 intersect each other exceeds 0° and is 60° or less. As described above, in a state where the plurality of fibers 21 are arranged, since fibers 21 tend to stretch along the arrangement direction of fibers 21, it is also possible to reduce the stress on the biological tissues and the microorganisms. Therefore, the biological tissues or the microorganisms easily grow along the arrangement direction of fibers 21.

Figure 16:
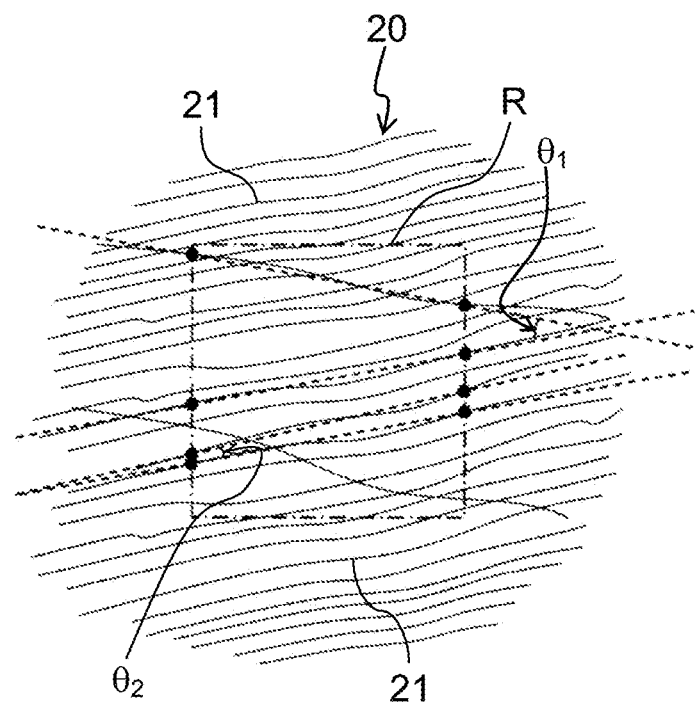
FIG. 16 is a schematic top view of a region of a part of the fiber assembly for explaining an arrangement of fibers.

Here, the average angle at which fibers 21 intersect each other can be determined from the intersection of fibers 21 in the average length direction. The average length direction of fibers 21 can be determined, for example, based on an SEM photograph of fiber assembly 20 when viewed from the normal direction thereof. FIG. 16 is a schematic top view of the fiber assembly for explaining the arrangement of the fibers. In FIG. 16, a state of fiber assembly 20 in the SEM photograph taken of fiber assembly 20 from the normal direction is simulated. A square region R having a predetermined size (for example, 100 μm×100 μm) is set by viewing fiber assembly 20 constituted by the plurality of fibers 21 from the normal direction. In this case, region R is determined so that 12 fibers 21 or more enter region R and 50% or more of fibers 21 located in region R intersect the opposing two sides of region R. In region R, the directions of straight lines (dotted lines in FIG. 16) connecting two points where certain fiber 21 intersects with the above-mentioned opposing two sides is set as the average length direction of fiber 21.

For an average angle at which fibers 21 intersect each other, for example, an angle (for example, θ1 in FIG. 16) at which the average length direction of respective fibers 21 intersects is obtained by selecting arbitrarily selected two fibers 21 from a plurality of (for example, 20) fibers 21 arbitrarily selected in region R. Two other fibers 21 are selected and an angle (for example, θ2 in FIG. 16) at which the average length direction of each fiber 21 intersects is obtained. Such an operation is performed on selected remaining fibers 21 (for example, 16). The average of the respective angles is calculated to be the average angle at which fibers 21 intersect each other.

A ratio of an area of fiber 21 occupying per unit area of fiber assembly 20 can be selected from 10% to 90%. For example, in a case where it is used for culturing cardiomyocytes or a potential measuring device, fiber assembly 20 is extremely thin, the ratio of fiber 21 occupying per unit area is 20% to 50%, and it is preferable that fiber 21 is uniformly dispersed at 30% to 40% and deposited. The ratio of the area of fiber 21 can be obtained by measuring glossiness with a gloss meter in a region of a predetermined area (for example, an elliptical shape having a minor axis of 3 mm and a major axis of 6 mm) in fiber assembly 20 on one main surface (for example, an upper surface) of fiber assembly 20, calculating the area occupied by fiber 21 based on a difference in glossiness between fiber 21 and regions other than fiber 21, and converting the area into the area ratio (%) per unit area.

Base Member

Base member 30 is not particularly limited and a base member which is utilized for a conventional medium (including a scaffold) can be used. As base member 30, a porous base member such as a resin film, an agar layer, a gelatin layer, or a nonwoven fabric, or a combination thereof, may be used depending on the biological tissue or the kind of the microorganisms to be cultured.

The material of the fiber contained in the nonwoven fabric is not particularly limited and examples thereof include glass fiber, cellulose, cellulose derivative (ether, ester, or the like), acrylic resin, polyolefin, polyester, polyamide, and the like. Examples of the polyolefin include polypropylene, polyethylene, and the like. Examples of the polyester include polyethylene terephthalate, polybutylene terephthalate, and the like. The fibers contained in the nonwoven fabric may contain one kind of these materials or may include two kinds or more.

Rotatable Winder

The configuration of rotatable winder 10 (rotation base body 11) is not particularly limited as long as it is rotatable, and may be a drum shape or a belt stretched by a plurality of rolls. In the latter case, at least one roll is driven to rotate and the belt is rotated. Examples of the material of rotatable winder 10 include metal materials, various resins, various rubbers, ceramics, and combinations thereof. In a case where rotatable winder 10 is a belt, the belt may be a metal belt or a resin belt. In the case where fibers 21 are spun by the electrospinning method, it is preferable that the resin belt has conductivity, and furthermore, a conductive member (for example, a metal member) is disposed on a back side of a portion of the resin belt facing nozzle 51. An outer shape of rotatable winder 10 may be, for example, a column or a prism.

2-1. Adhesive Applying Step (FIGS. 9B and 10)

It is preferable to provide an adhesive applying step of applying adhesive 4a to at least one of fiber assembly 20 and base member 30 before the transfer step described later. This is because the adhesive property between fiber assembly 20 and base member 30 is enhanced and peeling is suppressed.

In a case where adhesive 4a is applied to fiber assembly 20, the adhesive applying step (FIG. 9B) is performed after the deposition step (FIG. 9A) and before the transfer step (FIG. 9C). The kind of adhesive 4a is not particularly limited and examples thereof include a silicone resin, a hot Inch resin, an ultraviolet curable resin, and the like.

The silicone resin is also said to be a pressure sensitive adhesive, and by its adhesive property, fiber assembly 20 and base member 30 are bonded. Examples of the silicone resin include dimethyl silicone, methyl phenyl silicone, and the like. The hot melt resin is applied to fiber assembly 20 while being heated and is cooled to bond fiber assembly 20 and base member 30. The material of the hot melt resin is not particularly limited and examples thereof include polyester such as polyurethane (PU) and PET, copolymerized polyester such as urethane-modified copolyester, thermoplastic resin such as PA and polyolefin (for example, PP, PE) as a main component (component occupying 50% by mass or more).

The ultraviolet curable resin polymerizes and cures by irradiation with ultraviolet rays to bond fiber assembly 20 and base member 30. The type of ultraviolet curable resin is not particularly limited and examples thereof include acrylic resin, epoxy resin, and the like. In the case of using the ultraviolet curable resin, it is preferable to irradiate the ultraviolet curable resin with the ultraviolet before the transfer step to make the ultraviolet curable resin semi-cured. In this case, after fiber assembly 20 and base member 30 are in contact with each other in the transfer step, further ultraviolet irradiation is performed to completely cure the ultraviolet curable resin. Ultraviolet irradiation in the transfer step is performed, for example, from the side of base member 30.

The hot melt resin and the silicone resin are preferable as adhesive 4a in that a special step for curing can be omitted, and the silicone resin is preferable in that a heating device for melting the adhesive is unnecessary. The ultraviolet curable resin is preferable in that curing proceeds promptly. Adhesive 4a is applied, for example, by dispenser 55.

It is preferable that adhesive 4a is applied to a region corresponding to projection portion 10P of fiber assembly 20. In this case, fiber assembly 20 and base member 30 are pressed by projection portion 10P and pedestal 53 supported by XZ stage 52 in a state where adhesive 4a is interposed therebetween. Therefore, the adhesive property between fiber assembly 20 and base member 30 is improved. XZ stage 52 is capable of transporting pedestal 53 and base member 30 placed on pedestal 53 in a direction (X-axis direction) perpendicular to rotation axis A and a vertical direction (Z-axis direction).

Figure 10A:
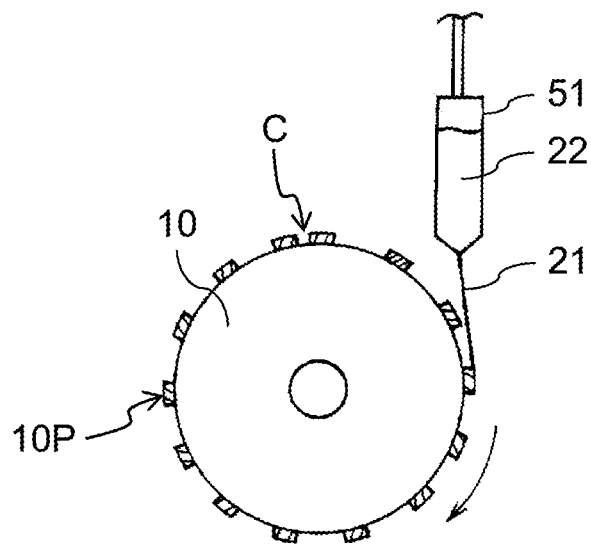
FIG. 10A is a side view schematically strafing a rotatable winder and a base member in each step of another producing method according to the disclosure.
Figure 10B:
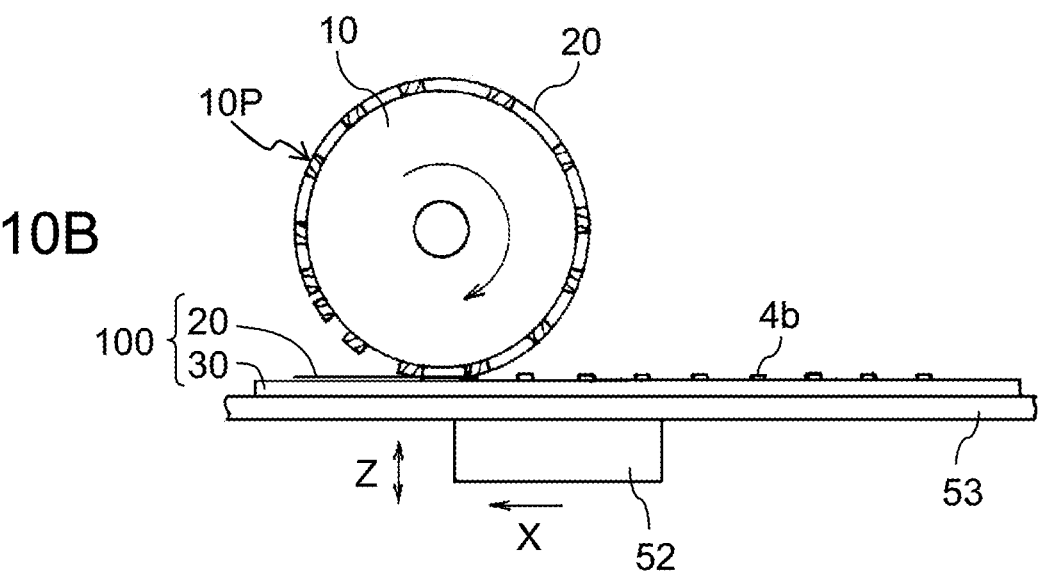
FIG. 10B is a side view schematically illustrating the rotatable winder and the base member in each step of another producing method according to the disclosure.

The pressure sensitive adhesive such as the silicone resin may be applied to fiber assembly 20 or base member 30 after being formed into a film-like shape. FIGS. 10A and 10B illustrate an adhesive applying step in a case of applying film-like pressure sensitive adhesive 4b to base member 30. In this case, timing of applying film-like pressure sensitive adhesive 4b to base member 30 is not particularly limited as long as it is before the transfer step. For example, film-like pressure sensitive adhesive 4b may be applied to base member 30 before being placed on pedestal 53. FIG. 10A corresponds to FIG. 9A.

An application amount of adhesive (4a or 4b) is not particularly limited. In particular, from the viewpoint of preventing the cultivation of the biological tissues or the microorganisms from inhibiting while securing the adhesive property between fiber assembly 20 and base member 30, it is preferably 0.5 to 100 mg/cm$^2$.

2-2. Heating Step (FIGS. 11A and 11B)

Before the transfer step, a heating step of heating at least one of fiber assembly 20 and base member 30 may be provided in place of the adhesive applying step or in addition to the adhesive applying step. Fiber assembly 20 is transferred to base member 30 in a softened state by heating fiber assembly 20 before the transfer step. Therefore, the adhesive property between fiber assembly 20 and base member 30 is improved. Heat is transferred to fiber assembly 20 and softened after the transfer by heating base member 30 before the transfer step. Therefore, the adhesive property between fiber assembly 20 and base member 30 is improved. In particular, the method of heating base member 30 is preferable in that deterioration of fibers 21 can be suppressed.

Figure 11A:
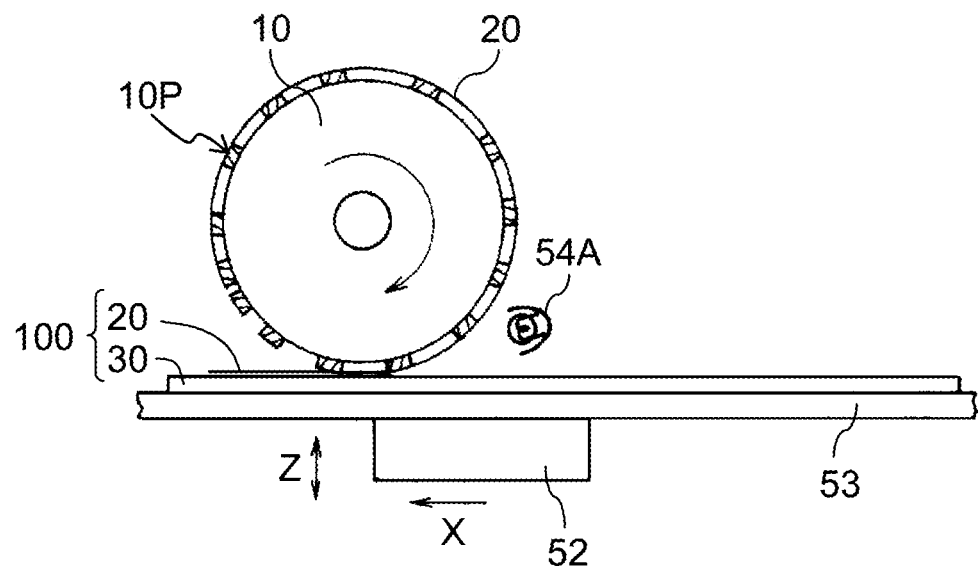
FIG. 11A is a side view schematically illustrating a rotatable winder and a base member in a heating step of a producing method according to the disclosure.

In a case where fiber assembly 20 is heated, for example, as illustrated in FIG. 11A, it is preferable to place heating device 54A in the vicinity of base member 30 so as to heat fiber assembly 20 immediately before transfer. In this case, fiber assembly 20 is heated, for example, in a line shape along rotation axis A. It is preferable that heating device 54A is a non-contact type in that the arrangement of fibers 21 can be maintained. Non-contact type heating device 54A is not particularly limited and a known one such as a halogen lamp may be appropriately selected. A heating temperature may be appropriately set in consideration of a softening point or a melting point of fiber 21 or the like. The heating temperature is adjusted, for example, so that fiber 21 becomes 80° C. to 140° C.

Figure 11B:
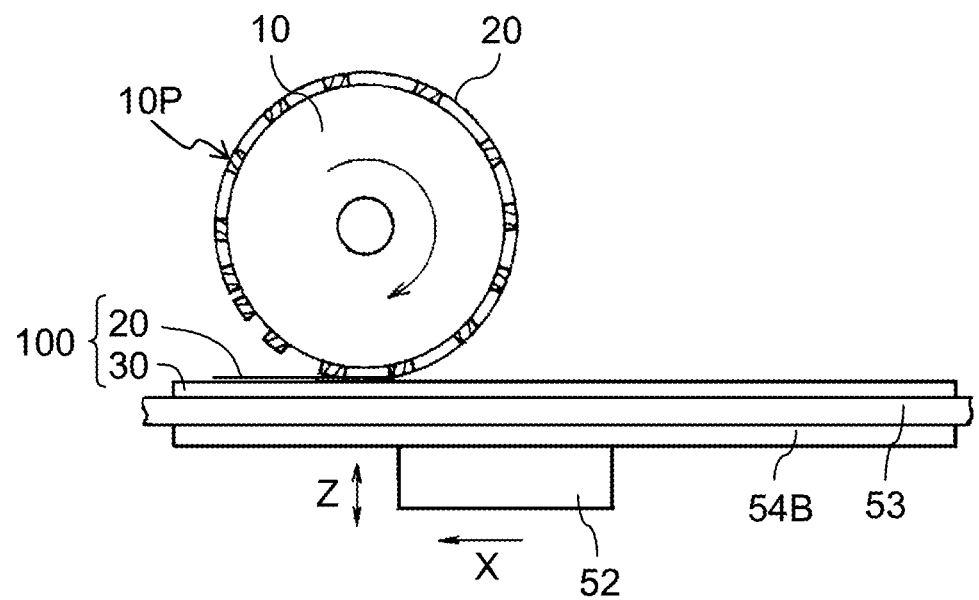
FIG. 11B is a side view schematically illustrating a rotatable winder and a base member in a heating step of another producing method according to the disclosure.

In a case where base member 30 is heated, for example as illustrated in FIG. 11B, heating device 54B is disposed between pedestal 53 on which base member 30 is placed and XZ stage 52. In this case, as heating device 54B, it is preferable to use a panel heater or the like capable of heating an entirety of base member 30. This is because temperature unevenness of base member 30 is suppressed. The heating temperature in this case may be appropriately set in consideration of the softening point or the melting point of fiber 21 or the like. The heating temperature is adjusted, for example, so that the surface of base member 30 becomes 80° C. to 140° C.

2-3. Plasma Processing Step (FIG. 12)

Before the transfer step, a plasma processing step of irradiating fiber assembly 20 with plasma may be provided instead of the adhesive applying step and the heating step, or in addition to the adhesive applying step and/or the heating step. The adhesive property between fiber assembly 20 and base member 30 is improved by irradiating at least the main surface of fiber assembly 20 which is in contact with base member 30 with the plasma. After transferring fiber assembly 20 to base member 30, plasma irradiation may be further performed on the main surface of fiber assembly 20 on a side opposite to base member 30. In the case of connecting fiber assembly 20 and an electrode (for example, a platinum electrode) in order to measure a change in a potential of the biological tissues or the microorganisms cultured in medium 100, adhesive property between the electrode and fiber assembly 20 is also improved by plasma irradiation.

Figure 12:
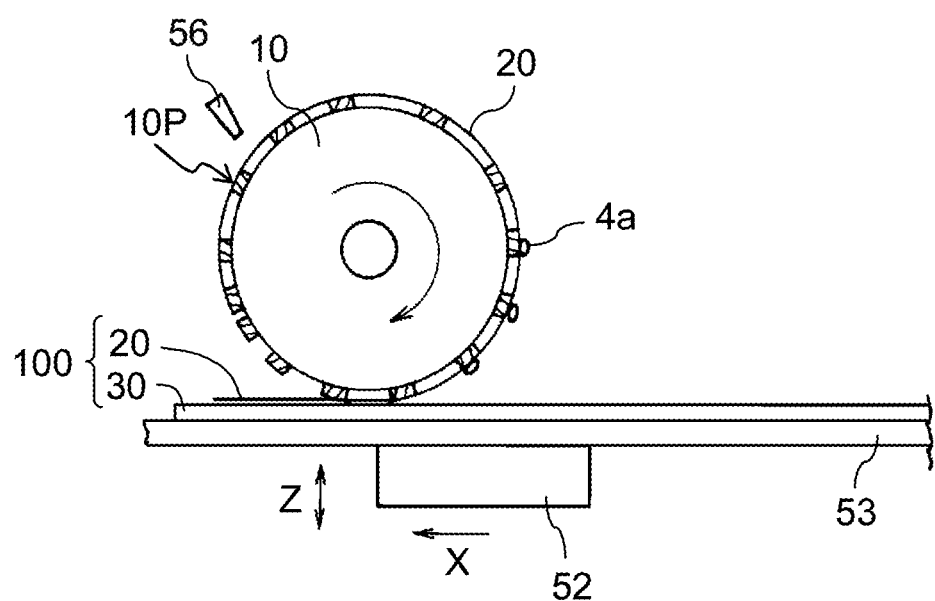
FIG. 12 is a side view schematically illustrating a rotatable winder and a base member in a plasma processing step of the producing method according to the disclosure.

In a case of irradiating fiber assembly 20 with the plasma, for example, as illustrated in FIG. 12, plasma irradiation device 56 is disposed to face the circumferential surface of rotatable winder 10. Plasma irradiation device 56 is not particularly limited, but in terms of being able to process without using a vacuum chamber, it is preferable to be a device capable of irradiating fiber assembly 20 with the plasma under atmospheric pressure. Conditions such as plasma irradiation are also not particularly limited and may be appropriately set so that fiber assembly 20 is not damaged.

3-1. Cutting Step (FIG. 9B)

Before the transfer step, fiber assembly 20 is cut at planned cutting point C in a state of being wound around rotatable winder 10. Planned cutting point C is set, for example, according to the shape of base member 30. Fiber assembly 20 is cut, for example, in a direction along rotation axis A. Fiber assembly 20 is transferred to base member 30 using the cut portion as a trigger. Cutting device 57 is not particularly limited and examples thereof include a long cutter and the like.

Figure 13A:
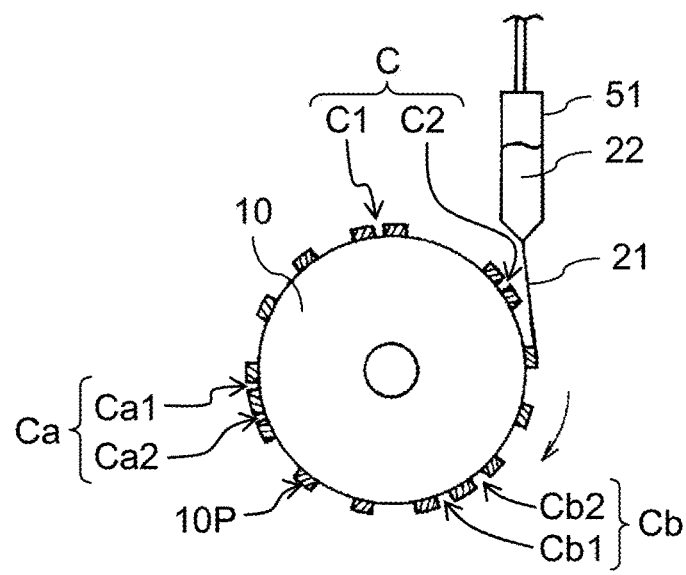
FIG. 13A is a side view schematically illustrating a rotatable winder and a base member in each step of further another producing method according to the disclosure.
Figure 13B:
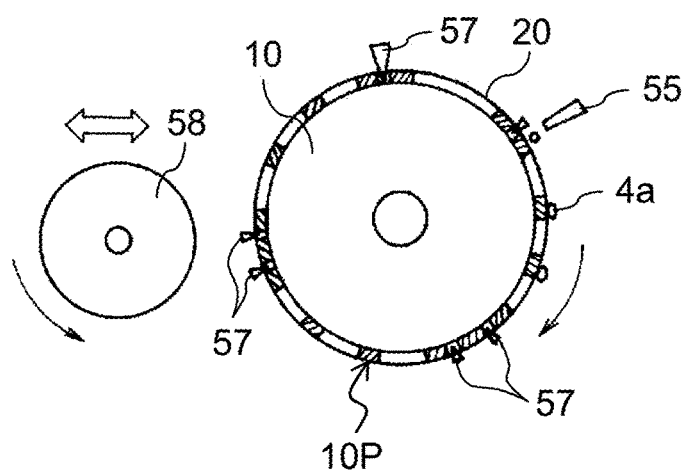
FIG. 13B is a side view schematically illustrating the rotatable winder and the base member in each step of further another producing method according to the disclosure.
Figure 13C:
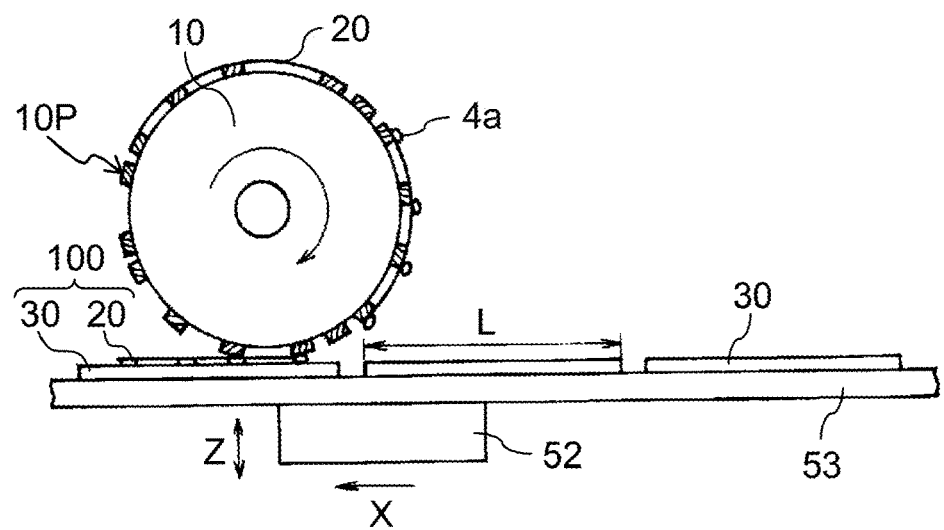
FIG. 13C is a side view schematically illustrating the rotatable winder and the base member in each step of further another producing method according to the disclosure.

In a case where length L (see FIG. 13C) of base member 30 in the direction (X-axis direction) perpendicular to rotation axis A is shorter than the circumferential length of rotatable winder 10, as illustrated in FIG. 13A, fiber assembly 20 may be cut to a length corresponding to length L at planned separation points Ca (Ca1 and Ca2) and Cb (Cb1 and Cb2) in addition to planned cutting point C (C1 and C2). Also, in this case, fiber assembly 20 is cut, for example, along the shape of base member 30. In FIG. 13, two planned separation points (Ca and Cb) are set, and three fiber assemblies 20 to be transferred to three base members 30 are formed on the circumferential surface of rotatable winder 10.

3-2. Cleaning Process (FIG. 13B)

Fiber assemblies 20 positioned between planned cutting points C1 and C2, between planned separation points Ca1 and Ca2, and between planned separation points Cb1 and Cb1 are unnecessary cut pieces not transferred to base member 30. As described above, in a case where unnecessary cut pieces are produced in the cutting step, it is preferable to provide a cleaning step of removing the cut pieces after the cutting step and before the transfer step. The process is simplified, the productivity is improved, and the quality of the obtained medium is enhanced.

The cleaning step is performed by adhesive member 58 (see FIG. 13B) having an adhesive layer. Examples of adhesive member 58 include an adhesive tape, the adhesive roll illustrated in FIG. 13B, and the like. The adhesive roll has an adhesive layer (not illustrated) on a circumferential surface thereof, and is capable of rotating, for example, in a direction opposite to rotatable winder 10. Adhesive member 58 is capable of approaching and retracting from rotatable winder 10. Adhesive member 58 is brought close to rotatable winder 10 at the timing when unnecessary cut pieces are opposed to adhesive member 58 by the rotation of rotatable winder 10. Therefore, unnecessary cut pieces are adhered to the adhesive layer of adhesive member 58 and removed from the circumferential surface of the rotatable winder 10. A material of the adhesive layer is not particularly limited and examples thereof include acryl adhesive and the like.

4. Transfer Step (FIG. 9C)

In this step, fiber assembly 20 is transferred to base member 30 while rotating rotatable winder 10. Therefore, medium 100 including fiber assembly 20 and base member 30 is obtained.

Base member 30 is placed on pedestal 53 supported by XZ stage 52 and is transported. In this case, it is preferable that base member 30 is transported in the X-axis direction at a relatively higher speed than the moving speed (circumferential speed) of the circumferential surface of rotatable winder 10. Therefore, fiber assembly 20 is transferred to base member 30 in a state where slackness is further suppressed.

Figure 14:
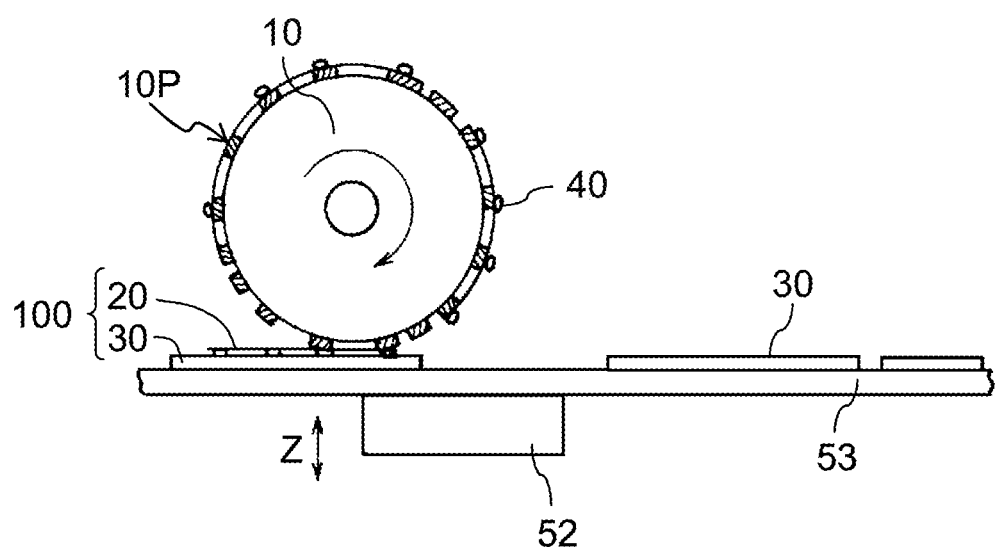
FIG. 14 is a side view schematically illustrating a rotatable winder and a base member in a transfer step of further another producing method according to the disclosure.

On the other hand, in the transfer step, base member 30 may be transported by the rotation of rotatable winder 10. That is, as illustrated in FIG. 14, after base member 30 is transported to a predetermined position, pedestal 53 is lifted to press base member 30 against rotatable winder 10. Next, rotatable winder 10 may be rotated to transport base member 30 by a frictional force generated between projection portion 10P and base member 30. Therefore, a relative transport speed of base member 30 becomes the same as the circumferential speed of rotatable winder 10, and the slackness of fiber assembly 20 is suppressed. Since alignment of base member 30 becomes easy, transfer misalignment of fiber assembly 20 is suppressed. After fiber assembly 20 is transferred, pedestal 53 is descended promptly and base member 30 is separated from rotatable winder 10.

Medium

Medium 100 includes fiber assembly 20 and base member 30. Base member 30 is mainly used for supporting fiber assembly 20. Fiber assembly 20 is capable of being used alone as a medium.

Since the medium and the fiber assembly obtained by the disclosure are provided with the fibers arranged in one direction, it is particularly useful as a medium for culturing the biological tissues or the microorganisms having a direction in growth.

What is claimed is:

1. A method for producing a medium comprising:
   forming a fiber assembly by discharging a raw material liquid of fibers from a nozzle to generate the fibers and depositing the fibers so as to surround a circumferential surface of a rotatable winder; and
   transferring the fiber assembly to a base member while rotating the rotatable winder,
   wherein the circumferential surface of the rotatable winder has a plurality of belt-shaped projection portions extending in a direction along a rotation axis of the rotatable winder.

2. The method for producing a medium of claim 1,
   wherein at least a contact portion of the projection portions with the fibers has a silicone rubber layer.

3. The method for producing a medium of claim 1,
   wherein the rotatable winder has a rotation base body and a supporting sheet wound around the rotation base body, and
   wherein the projection portions are formed of a silicone rubber disposed on the supporting sheet.

4. The method for producing a medium of claim 1, further comprising:
   applying adhesive to at least one of the fiber assembly and the base member before the transferring.

5. The method for producing a medium of claim 4,
   wherein the adhesive is a film-shaped pressure sensitive adhesive.

6. The method for producing a medium of claim 4,
   wherein the adhesive is a silicone resin, a hot melt resin, or an ultraviolet curable resin.

7. The method for producing a medium of claim 1, further comprising:

heating at least one of the fiber assembly and the base member before the transferring.

8. The method for producing a medium of claim 1, further comprising:
irradiating the fiber assembly with plasma.

9. The method for producing a medium of claim 1, wherein the circumferential surface of the rotatable winder includes ribs extending in a direction intersecting the rotation axis.

10. The method for producing a medium of claim 1, wherein in the transferring, the base member is transported by the rotation of the rotatable winder.

11. The method for producing a medium of claim 1, wherein in the transferring, the base member is transported at a speed faster than a moving speed of the circumferential surface of the rotatable winder.

12. The method for producing a medium of claim 1, wherein a length L of the base member in a direction perpendicular to the rotation axis is shorter than a circumferential length of the rotatable winder, and
wherein the method further comprises:
cutting the fiber assembly to a length corresponding to the length L before the transferring.

13. The method for producing a medium of claim 12, further comprising:
removing cut pieces by bringing an adhesive member including an adhesive layer to abut against the fiber assembly after the cutting.

14. The method for producing a medium of claim 1, wherein the rotatable winder has a rotation base body, and
wherein a plurality of grooves extending in the direction along the rotation axis of the rotation base body are formed on a surface of the rotation base body, and a part of the projection portions is formed between the grooves adjacent to each other.

15. A method for producing a fiber assembly including a plurality of fibers arranged in one direction, the method comprising:
preparing a raw material liquid of the fibers; and
depositing the fibers generated by discharging the raw material liquid of the fibers from a nozzle so as to surround a circumferential surface of a rotatable winder, wherein the circumferential surface of the winder has a plurality of belt-shaped projection portions extending in a direction along a rotation axis of the rotatable winder.

\* \* \* \* \*